US006355644B1

(12) United States Patent
Zhao et al.

(10) Patent No.: US 6,355,644 B1
(45) Date of Patent: Mar. 12, 2002

(54) BENZYLPIPERAZINYL-INDOLINYLETHANONES

(75) Inventors: He Zhao, Branford; Andrew Thurkauf, Danbury, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/594,040

(22) Filed: Jun. 14, 2000

Related U.S. Application Data
(60) Provisional application No. 60/138,974, filed on Jun. 14, 1999.

(51) Int. Cl.[7] ................. A61K 31/496; C07D 403/06
(52) U.S. Cl. ................. 514/254.08; 514/254.09; 544/372; 544/373; 435/7.21; 436/501; 436/503; 436/504; 206/568; 206/570
(58) Field of Search .................. 544/373, 372; 514/254.09, 254.08

(56) References Cited

U.S. PATENT DOCUMENTS 2,909,523 A  10/1959  Bach, Jr. et al.
6,084,098 A * 7/2000 Kover et al. ............... 544/373

FOREIGN PATENT DOCUMENTS

| WO | WO 98/28293 | 7/1998 |
| WO | WO 99/21848 | 5/1999 |
| WO | WO 99/43670 | 9/1999 |

OTHER PUBLICATIONS

Bertini Gross, (J. Org. Chem. 62, 7679 (1997)).
VanTol et al., *Nature*, vol. 350, pp. 610–614, 1991.*

* cited by examiner

*Primary Examiner*—Emily Bernhardt
(74) *Attorney, Agent, or Firm*—McDonnell Boehnen Hulbert & Berghoff

(57) ABSTRACT

Disclosed are benzylpiperazinyl-indolinylethanone compounds which are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents. Pharmaceutical compositions, including packaged pharmaceutical compositions, are further provided. Compounds of the invention are also useful as probes for the localization of $GABA_A$ receptors in tissue samples.

43 Claims, No Drawings

BENZYLPIPERAZINYL-INDOLINYLETHANONES

This application claims priority to provisional application no. 60/138,974 filed Jun. 14, 1999, which is hereby incorporated by reference in its entirety.

BACKGROUND OF THE INVENTION

1. Field of the Invention

This invention relates to benzylpiperazinyl-indolinylethanones, and to compounds that bind to dopamine receptors. This invention also relates to pharmaceutical compositions comprising such compounds and to the treatment of central nervous system (CNS) diseases, particularly the treatment or prevention of psychotic disorders such as schizophrenia. Additionally this invention relates to the use of compounds as probes for the localization of dopamine receptors in tissue sections.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has been identified and cloned. Its unique localization in limbic brain areas and its differential recognition of various antipsychotics suggest that the $D_4$ receptor may play a major role in the etiology of schizophrenia. The dopamine $D_4$ receptor shares sequence homology with dopamine $D_2$ and $D_3$ receptors, however the $D_4$ receptor possesses a unique pharmacological profile. Selective $D_4$ antagonists, including the marketed antipsychotic chlozapine, are considered effective antipsychotics free from the neurological side effects displayed by conventional neuroleptics. Compounds that possess a 10-fold or more higher affinity for dopamine $D_4$ receptors than $D_2$ receptors are considered particularly desirable as antipsychotics.

Since dopamine $D_4$ receptors are concentrated in the limbic system which controls cognition and emotion, compounds which interact with these receptors have utility in the treatment of cognitive disorders. Such disorders include the cognitive deficits which are a significant component of the negative symptoms (social withdrawal and unresponsiveness) of schizophrenia. Other disorders involving memory impairment or attention deficit disorder can also be treated with compound that interact specifically with the dopamine $D_4$ receptor subtype.

SUMMARY OF THE INVENTION

This invention provides benzylpiperazinyl-indolinylethanone compounds that bind, preferably with high affinity and selectivity, to the $D_4$ receptor subtype, including human $D_4$ receptors. These compounds are therefore useful in treatment of a variety of neurospychological disorders, such as, for example, schizophrenia, psychotic depression and mania. Other dopamine-mediated diseases such as Parkinsonism and tardive dyskinesias can also be treated directly or indirectly by modulation of $D_4$ receptors.

In another aspect, the invention provides intermediates useful in the preparation of compounds of Formula I. The invention also provides methods for preparing the compounds of the invention.

Thus, the invention provides compounds of Formula I (shown below), and pharmaceutical compositions comprising compounds of Formula I.

The invention further comprises methods of treating patients suffering from CNS disorder with an effective amount of a compound of the invention. The patient may be a human or other mammal. Treatment of humans, domesticated companion animals (pets) or livestock animals suffering from CNS disorder with an effective amount of a compound of the invention is encompassed by the invention. Particularly methods for the treatment and/or prevention of neuropsychochological or affective disorders, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents are included. In addition, the compounds of the invention are useful in treatment of depression, memory-impairment or Alzheimer's disease by modulation of $D_4$ receptors which selectively exist in limbic areas known to control emotion and cognitive functions. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

Accordingly, a broad embodiment of the invention is directed to a compound of Formula I:

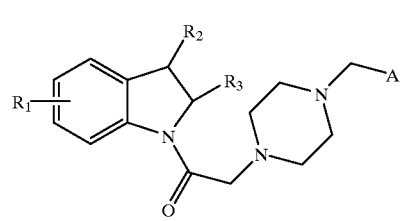

wherein

A represents a phenyl group optionally substituted with up to four groups independently selected from halogen, hydroxy, amino, mono- or di($C_1$–$C_6$) hydrocarbylamino, aminosulfonyl, $C_1$–$C_6$ hydrocarbylaminosulfonyl, di($C_1$–$C_6$) hydrocarbylaminosulfonyl, cyano, nitro, cyclohydrocarbylhydrocarbyl, trifluoromethyl, $C_1$–$C_6$ hydrocarbyl, trifluoromethoxy, $C_3$–$C_6$ cyclohydrocarbyl, and $C_1$–$C_6$ alkoxy;

$R_1$ represents hydrogen, halogen, hydroxy, amino, aminosulfonyl, $C_1$–$C_6$ hydrocarbylaminosulfonyl, di($C_1$–$C_6$)hydrocarbylaminosulfonyl, cyano, nitro, trifluoromethyl, trifluoromethoxy, $C_1$–$C_6$ hydrocarbyl, cyclohydrocarbylhydrocarbyl, $C_3$–$C_6$ cyclohydrocarbyl, and $C_1$–$C_6$ alkoxy; and $R_2$ is $C_1$–$C_6$ hydrocarbyl and $R_3$ is hydrogen or $C_1$–$C_6$ hydrocarbyl; or $R_2$ is hydrogen and $R_3$ is mono, di, or trifluoromethyl, hydroxy($C_1$–$C_3$)hydrocarbyl, $C_1$–$C_6$ alkoxy($C_1$–$C_3$) hydrocarbyl, mono or di($C_1$–$C_6$)hydrocarbylamino ($C_1$–$C_3$)hydrocarbyl, carboxamido, mono or dihydrocarbylaminocarbonyl, aminohydrocarbyl, carboxy, $C_1$–$C_6$ alkoxycarbonyl, carbamoyl, mono or di($C_1$–$C_6$)hydrocarbylcarbamoyl, aryl($C_1$–$C_6$) hydrocarbylcarbamoyl, N,N-(aryl($C_1$–$C_6$)hydrocarbyl) (($C_1$–$C_6$)hydrocarbyl)carbamoyl, or alkenyl; or $R_2$ and $R_3$ taken together with the atoms to which they are attached form a saturated ring having from 5 to 7 carbon atoms; or $R_3$ is hydrogen and $R_2$ is mono, di, or trifluoromethyl, hydroxy ($C_1$–$C_3$)hydrocarbyl, $C_1$–$C_6$ alkoxy($C_1$–$C_3$) hydrocarbyl, mono or di($C_1$–$C_6$)hydrocarbylamino ($C_1$–$C_3$)hydrocarbyl, carboxamido, mono or dihydrocarbylaminocarbonyl, aminohydrocarbyl, carboxy, $C_1$–$C_6$ alkoxycarbonyl, carbamoyl, mono or di($C_1$–$C_6$)hydrocarbylcarbamoyl, aryl ($C_1$–$C_6$) hydrocarbylcarbamoyl, N,N-(aryl ($C_1$–$C_6$) hydrocarbyl) (($C_1$–$C_6$)hydrocarbyl)carbamoyl, or alkenyl.

DETAILED DESCRIPTION OF THE INVENTION

The invention encompasses the compounds of Formula I described above.

Preferred compounds of Formula I are those where A is a group of the formula IA:

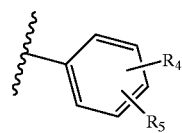

Formula IA where $R_4$ and $R_5$ independently represent hydrogen, halogen, hydroxy, amino, mono- or di($C_1$–$C_6$)alkylamino, aminosulfonyl, $C_1$–$C_6$ alkylaminosulfonyl, di($C_1$–$C_6$) alkylaminosulfonyl, cyano, nitro, trifluoromethoxy, $C_1$–$C_6$ alkyl, or $C_1$–$C_6$ alkoxy.

Preferably $R_4$ and $R_5$ independently represent hydrogen, halogen, $C_1$–$C_6$ alkoxy, or $C_1$–$C_6$ alkyl.

The most preferred compounds of Formula I are those where only one of $R_4$ and $R_5$ is a non-hydrogen substituent, most preferably fluoro, chloro, bromo, methyl, ethyl, or amino. Highly preferred of these latter compounds are those where the fluoro, chloro, or methyl group is in the para position of the phenyl ring.

Particularly preferred compounds of Formula I are those where $R_1$ is hydrogen.

A first set of preferred compounds of the invention are those where $R_3$ and $R_2$ in Formula I are hydrogen and $C_1$–$C_6$ alkyl, respectively. Such compounds are represented by Formula II.

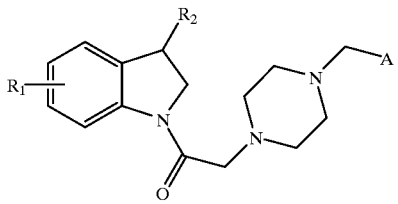

II wherein $R_1$ and A are as defined above for Formula I and $R_2$ is $C_1$–$C_6$ alkyl.

Preferred compounds of II are those where A is a group of the formula IA and $R_4$ and $R_5$ are as defined above for Formula IA. More preferred compounds of Formula II are those where A represents a group of Formula IA and $R_4$ and $R_5$ independently represent hydrogen, halogen, $C_1$–$C_6$ alkoxy, or $C_1$–$C_6$ alkyl. Particularly preferred compounds of Formula II are those where $R_2$ is $C_1$–$C_3$ alkyl; even more preferred compounds of II are those where $R_2$ is methyl.

The most preferred compounds of Formula II are those where both of $R_2$ and $R_3$ are methyl and only one of $R_4$ and $R_5$ is a non-hydrogen substituent, most preferably fluoro, chloro, or methyl. Highly preferred of these latter compounds are those where the fluoro, chloro, or methyl group is in the para position of the phenyl ring.

The most preferred compounds of Formula II have the following stereochemistry at $R_2$:

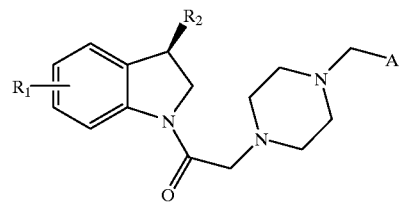

where $R_2$ is a non-hydrogen substituent.

Another set of preferred compounds of Formula I are those where both $R_2$ and $R_3$ are $C_1$–$C_6$ alkyl. Such compounds are identified hereinafter as compounds of Formula III.

Preferred compounds of III are those where A is a group of the formula IA and $R_4$ and $R_5$ are as defined above for Formula IA. More preferred compounds of Formula III are those where A represents a group of Formula IA and $R_4$ and $R_5$ independently represent hydrogen, halogen, $C_1$–$C_6$ alkoxy, or $C_1$–$C_6$ alkyl. Particularly preferred compounds of Formula III are those where $R_2$ and $R_3$ independently represent $C_1$–$C_3$ alkyl; even more preferred compounds of III are those where both $R_2$ and $R_3$ are methyl.

Another preferred set of compounds of Formula I are those where $R_2$ and $R_3$ together form a straight $C_3$–$C_5$ alkylene group, i.e., where $R_2$ and $R_3$ together with the atoms to which they are attached form a saturated ring having from 5 to 7 carbon atoms. Such compounds are represented herein by Formula IV:

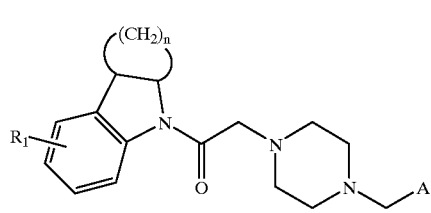

IV wherein $R_1$ and A are as defined above for Formula I and n is an integer of from 3–5.

Preferred compounds of IV are those where A is a group of the formula IA and $R_4$ and $R_5$ are as defined above for Formula IA. More preferred compounds of Formula IV are those where A represents a group of Formula IA and $R_4$ and $R_5$ independently represent hydrogen, halogen, $C_1$–$C_6$ alkoxy, or $C_1$–$C_6$ alkyl. Particularly preferred compounds of Formula IV are those where $R_2$ and $R_3$ represent a butylene group. The resulting ring system may be identified as a 5,6,7,8,9,4b,8a-heptahydro-4aH -carbazole, shown below as Formula IV-A.

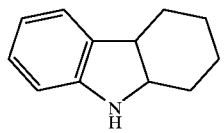

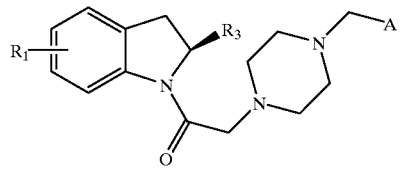

The most preferred compounds of Formula IV are those where only one of $R_4$ and $R_5$ is a non-hydrogen substituent, most preferably fluoro, chloro, or methyl. Highly preferred of these latter compounds are those where the fluoro, chloro, or methyl group is in the para position of the phenyl ring.

The most preferred compounds of Formulas III and IV have the following stereochemistry at $R_2$ and $R_3$:

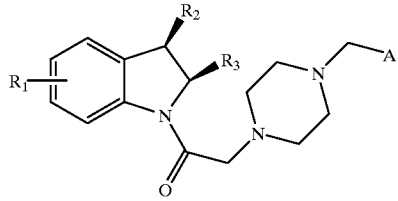

In this formula, neither of $R_2$ and $R_3$ is hydrogen.

Another preferred set of compounds of the invention are those where $R_2$ is hydrogen and $R_3$ is mono, di, or trifluoromethyl, hydroxymethyl, $C_1$–$C_6$ alkoxymethyl, di($C_1$–$C_6$)alkylaminomethyl, carboxy, $C_1$–$C_6$ alkoxycarbonyl, carbamoyl, mono or di($C_1$–$C_6$) alkylcarbamoyl, aryl($C_1$–$C_6$)alkylcarbamoyl, N-(aryl ($C_1$–$C_6$)alkyl)-N-(($C_1$–$C_6$)alkyl)carbamoyl, or vinyl. Such compounds are generally represented by Formula V:

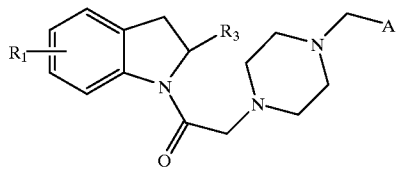

wherein $R_1$ and A are as defined above for Formula I and $R_3$ is mono, di, or trifluoromethyl, hydroxymethyl, $C_1$–$C_6$ alkoxymethyl, di($C_1$–$C_6$)alkylaminomethyl, carboxy, $C_1$–$C_6$ alkoxycarbonyl, carbamoyl, mono or di($C_1$–$C_6$) alkylcarbamoyl, aryl($C_1$–$C_6$)alkylcarbamoyl, N-(aryl ($C_1$–$C_6$)alkyl)-N-(($C_1$–$C_6$)alkyl)carbamoyl, or vinyl.

Preferred compounds of V are those where A is a group of the formula IA and $R_4$ and $R_5$ are as defined above for Formula IA. More preferred compounds of Formula V are those where A represents a group of Formula IA and $R_4$ and $R_5$ independently represent hydrogen, halogen, $C_1$–$C_5$ alkoxy, or $C_1$–$C_6$ alkyl.

The most preferred compounds of Formula V are those where $R_3$ is $C_1$–$C_3$ alkoxycarbonyl or vinyl and only one of $R_4$ and $R_5$ is a non-hydrogen substituent, most preferably fluoro, chloro, or methyl. Highly preferred of these latter compounds are those where the fluoro, chloro, or methyl group is in the para position of the phenyl ring. A particularly preferred alkoxycarbonyl group is methoxycarbonyl.

The most preferred compounds of Formula V have the following stereochemistry at $R_3$:

The invention also provides intermediates useful in preparing compounds of Formula I. These intermediates have Formula VI.

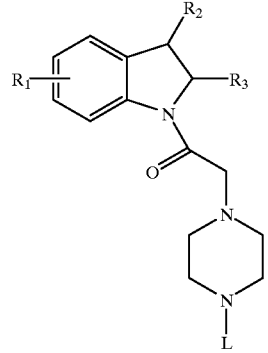

In Formula VI, $R_1$, $R_2$, and $R_3$ are as defined above for Formula I. L is hydrogen, a nitrogen protecting group, or —$CH_2$—A. $R_3$ is carboxy, alkoxycarbonyl, aminocarbonyl, mono or dialkylaminocarbonyl, and carboxaldehyde.

The compounds of this invention may contain one or more asymmetric carbon atoms, so that the compounds can exist in different stereoisomeric forms. These compounds can be, for example, mixtures of diastereomers, or racemates or resolved enantiomers. Single enantiomers can be obtained as pure compounds or in enantiomeric excess by asymmetric synthesis or by resolution of the racemate. Resolution of the racemate can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include, but are not limited to salts inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts.

The present invention also encompasses prodrugs of the compounds of Formula I, e.g., acylated compounds and esters of Formula I. Those skilled in the art will recognize various synthetic methodologies which may be employed to prepare non-toxic pharmaceutically acceptable addition salts and prodrugs of the compounds encompassed by Formula I.

Where a compound exists in various tautomeric forms, the invention is not limited to any one of the specific tautormers. The invention includes all tautomeric forms of a compound.

Representative compounds of the invention are shown below in Table 1.

TABLE 1

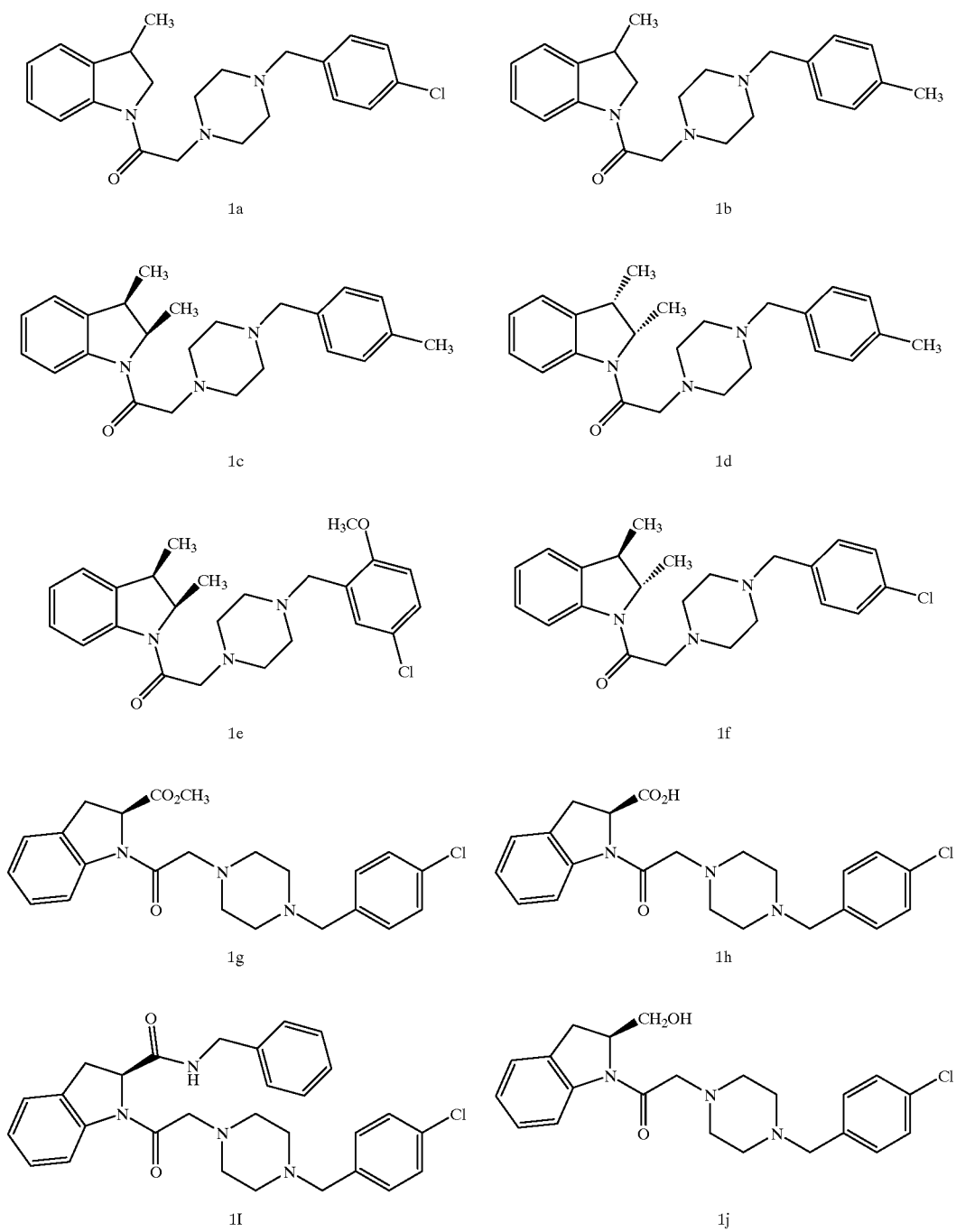

TABLE 1-continued

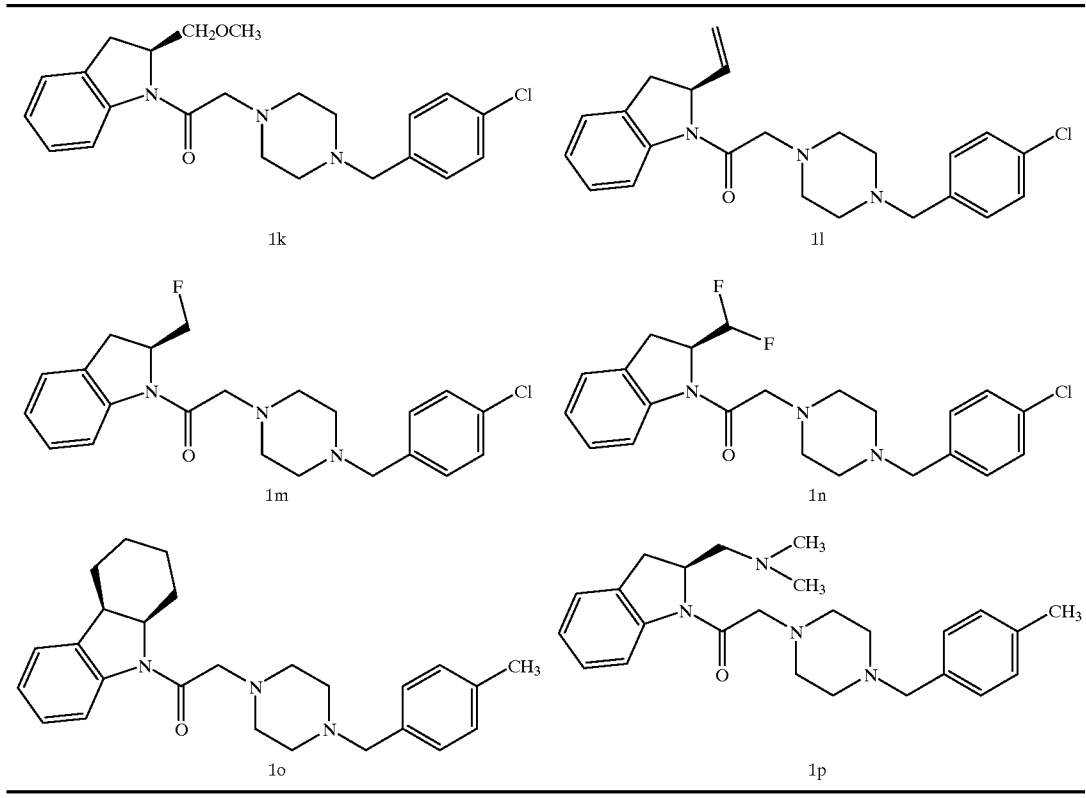

Compounds 1c, 1g, 1l and 1o are particularly preferred embodiments of the present invention because of their potency in binding to dopamine receptor subtypes.

This invention provides benzylpiperazinyl-indolinylethanone compounds that bind with high affinity to dopamine receptors, particularly dopamine $D_4$ receptors, including human dopamine $D_4$ receptors. This invention also includes compounds that bind with high selectivity to dopamine receptors, particularly dopamine $D_4$ receptors, including human dopamine $D_4$ receptors. Without wishing to be bound to any particular theory, it is believed that the interaction of the compounds of the invention with the dopamine $D_4$ receptor results in the pharmaceutical utility of these compounds.

The invention further comprises methods of treating patients suffering from a CNS disorder with an amount of a compound of the invention sufficient to alter the symptoms of the CNS disorder.

The diseases, conditions and disorders that can be treated using compounds and compositions according to the invention include, but are not limited to, schizophrenia, psychotic depression, mania, and the extrapyramidyl side effects associated with the use of a neuroleptic agent. Other dopamine-mediated disease such as Parkinsonism and tardive dyskinesias can also be treat directly or indirectly by modulation of dopamine receptors. Compounds of the invention are also useful in the treatment of depression, memory-impairment or Alzheimer's disease by modulation of $D_4$ receptors since these receptors are localized in areas known to control emotion and cognitive functions.

The invention also provides pharmaceutical compositions comprising compounds of the invention, including packaged pharmaceutical compositions, for treating disorders responsive to dopamine receptor modulation, especially dopamine $D_4$ receptor modulation, e.g., treatment of schizophrenia, depression, tardive diskinesia or cognitive impairment by dopamine $D_4$ receptor modulation. The packaged pharmaceutical compositions include a container holding a defined quantity or unit dose, e.g., a therapeutically effective amount, of at least one compound of the invention and instructions (e.g., labeling) indicating how the compound is to be used in the patient, e.g., for treating a disorder responsive to dopamine receptor modulation.

The present invention also pertains to methods of inhibiting the binding of dopamine to dopamine $D_4$ receptors which methods involve contacting a compound of the invention with cells expressing dopamine $D_4$ receptors, wherein the compound is present at a concentration sufficient to inhibit dopamine binding to dopamine $D_4$ receptors in vitro. This method includes inhibiting the binding of dopamine to dopamine $D_4$ receptors in vivo, e.g., in a patient given an amount of a compound of Formula I that would be sufficient to inhibit the binding of dopamine to dopamine $D_4$ receptors in vitro. The amount of a compound that would be sufficient to inhibit the binding of dopamine to the dopamine $D_4$ receptor may be readily determined via a dopamine receptor binding assay, such as the assay described in Example 11. The dopamine receptors used to determine in vitro binding may be obtained from a variety of sources, for example from preparations of rat striatal homogenates or from cells expressing cloned human or monkey dopamine $D_4$ receptors, especially CHO (Chinese hamster ovary) cells expressing such receptors.

The compounds of this invention and labeled derivatives thereof are also useful as standards and reagents in determining the ability of a potential pharmaceutical to bind to the dopamine $D_4$ receptor.

Radiolabeled derivatives of the compounds of the invention are also useful as radiotracers for positron emission tomography (PET) imaging or for single photon emission computerized tomography (SPECT).

Definitions

Where the compounds of the present invention have asymmetric centers, the invention includes all of the optical isomers and mixtures thereof.

Compounds with carbon-carbon double bonds may occur in Z- and E- forms, and all the isomers of the compounds are included in the invention.

When any variable (e.g. $C_{1-6}$ alkyl, $C_{1-8}$ alkyl, A, $R_1$, $R_2$, or $R_3$) occurs more than one time in any formula herein, its definition at each occurrence is independent of its definition at every other occurrence.

By "$C_1$–$C_6$ alkyl" in the present invention is meant straight or branched chain alkyl groups having 1–6 carbon atoms. Examples of alkyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "$C_1$–$C_6$ hydrocarbyl" in the present invention is meant straight or branched chain alkyl groups having 1–6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentenyl, 2-butenyl, 3-pentynyl, and propargyl. When reference is made herein to $C_1$–$C_6$ hydrocarbyl containing one or two double or triple bonds it is understood that at least two carbons are present in the alkyl for one double or triple bond, and at least four carbons for two double or triple bonds.

By "$C_1$–$C_6$ alkoxy" or "lower alkoxy" in the present invention is meant an alkyl group of indicated number of carbon atoms attached to the parent molecular moiety through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. Preferred alkoxy groups herein are $C_1$–$C_4$ alkoxy groups.

The term "cycloalkylalkyl," as used herein, refers to a $C_3$–$C_7$ cycloalkyl group attached to the parent molecular moiety through an alkyl group, as defined above. Examples of cycloalkylalkyl groups include cyclopropylmethyl and cyclopentylethyl.

The term "halogen" indicates fluorine, chlorine, bromine, or iodine.

The term "nitrogen protecting group," as used herein, refers to groups known in the art that are readily introduced on to and removed from a nitrogen. Examples of nitrogen protecting groups include Boc, Cbz, benzoyl, and benzyl. See also "Protective Groups in Organic Synthesis", 2nd Ed., Greene, T. W. and related publications.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the compounds of the invention may also be added to the animal's feed or drinking water. It will be convenient to formulate these animal feed and drinking water compositions so that the animal consumes an appropriate quantity, e.g., a therapeutically effective amount, of the compound in its diet. It will also be convenient to present the compound in a composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of schizophrenia, depression, or cognitive impairment a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have desirable pharmacological properties that include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

Preparation of Compounds

A representative synthesis of the compounds of the invention is presented in Schemes 1, 2, 3, 4, 5, and 6. Those having skill in the art will recognize that the starting materials and reaction conditions may be varied, the order of the steps may be altered and additional steps may be employed to produce compounds encompassed by the present invention.

Scheme 1
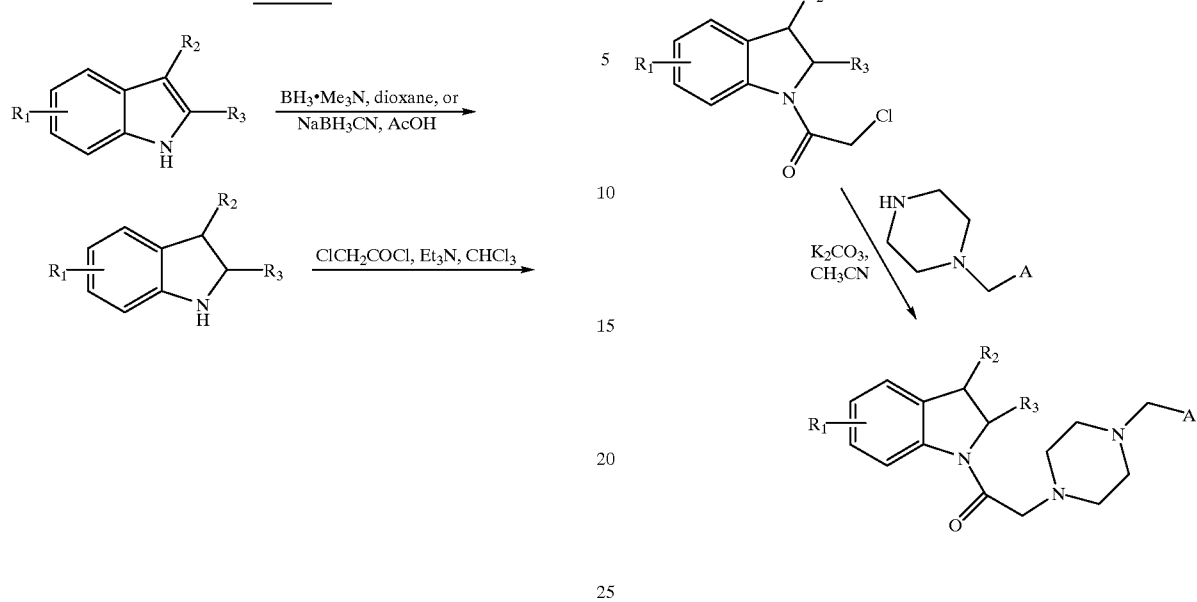
Scheme 2
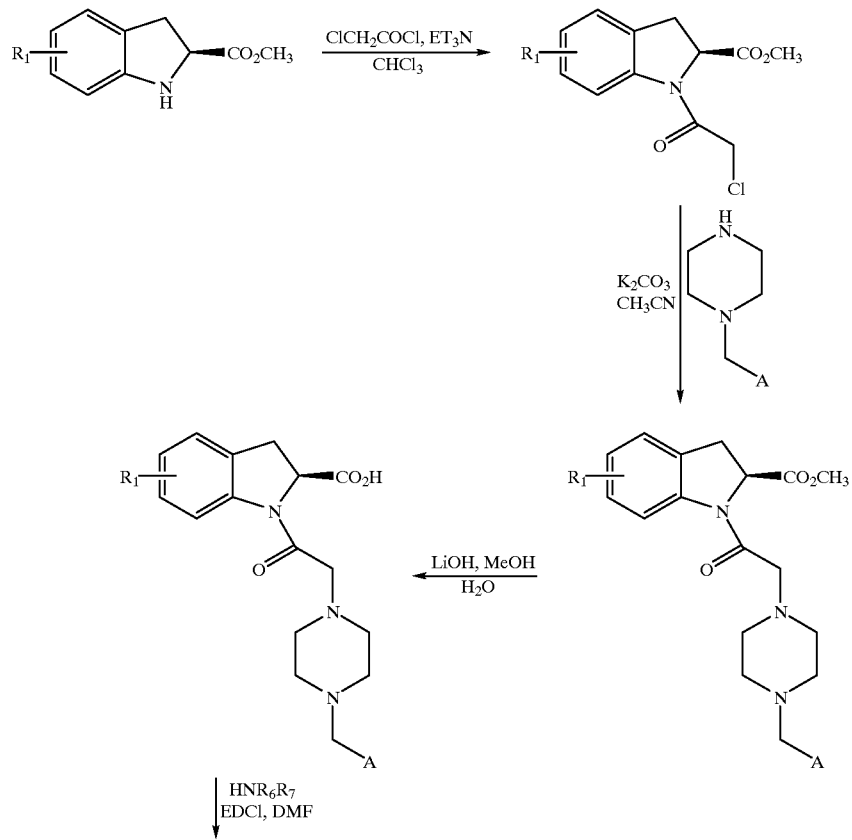

-continued
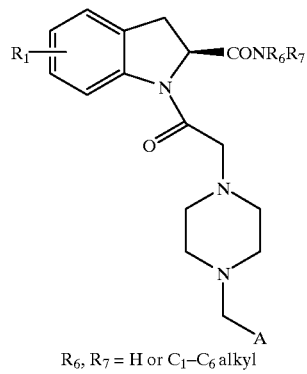
$R_6$, $R_7$ = H or $C_1$–$C_6$ alkyl
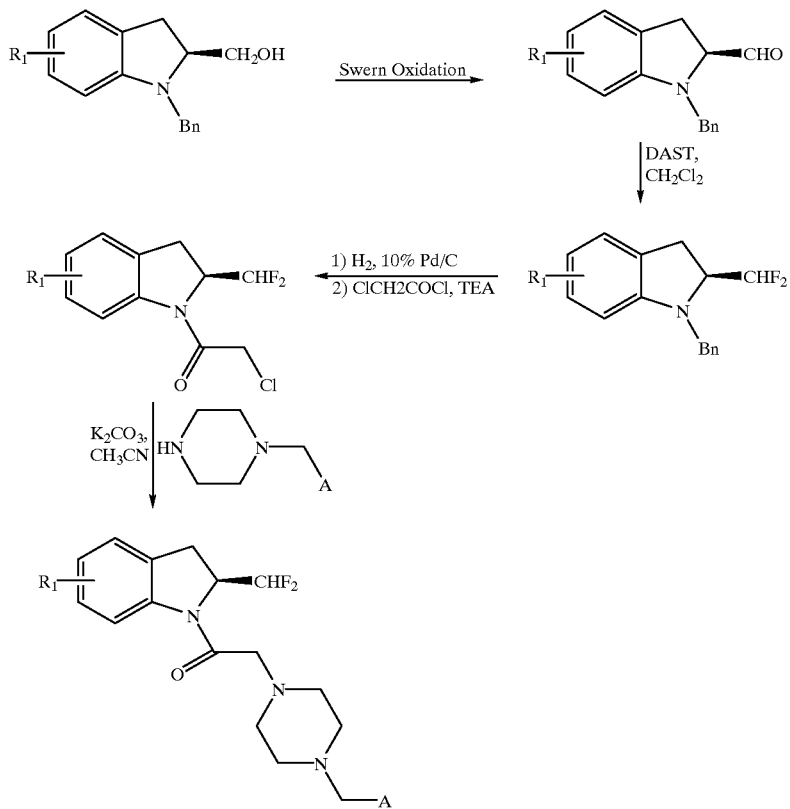

Scheme 4
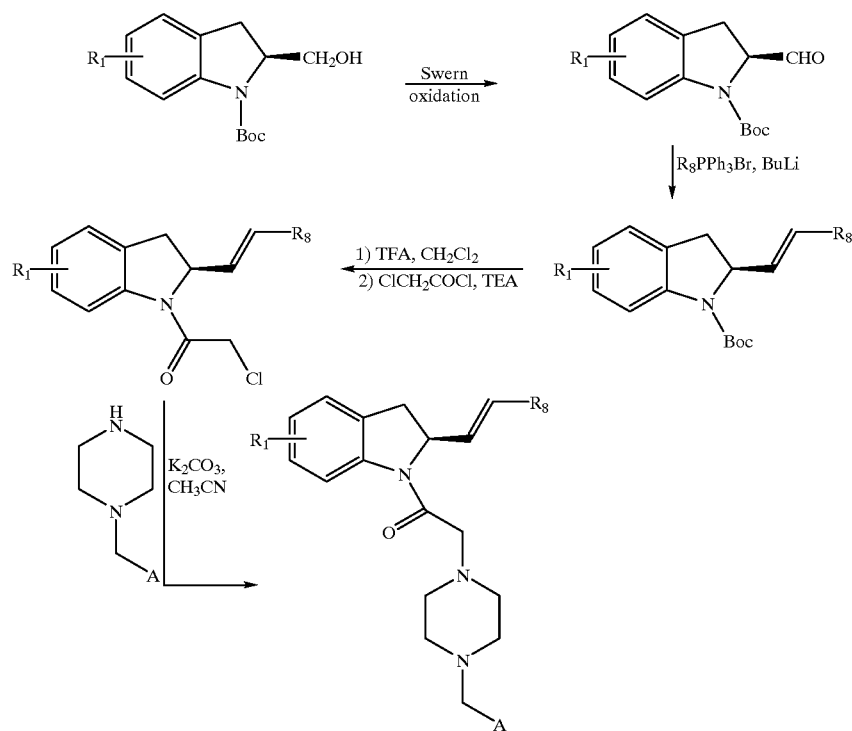
35
Scheme 5
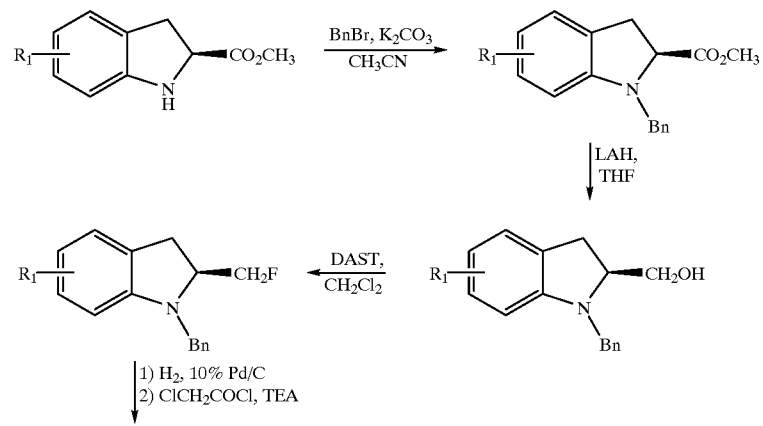

-continued

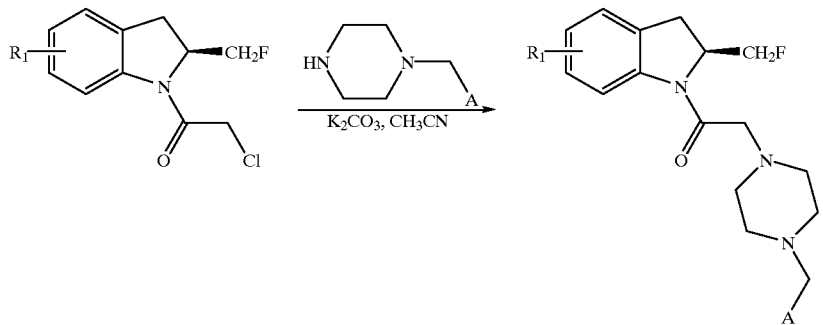

Scheme 6

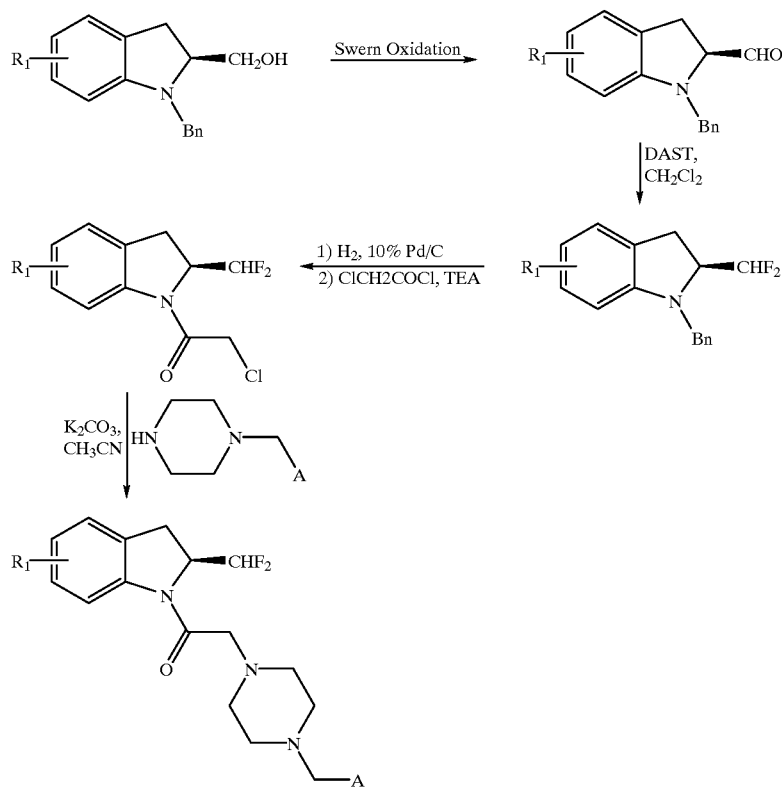

In the above schemes, $R_1$, $R_2$, $R_3$, and A are as defined for Formula I.

The starting materials used herein are either commercially available, known, or capable of being prepared by methods known in the art.

Unless otherwise stated, all standard commercial grade starting materials are used without further purification. In some cases, protection of reactive functionalities may be necessary to achieve some of the above transformations. In general, the need for such protecting groups as well as the conditions necessary to attach and remove such groups will be apparent to those skilled in the art of organic synthesis. See also "Protective Groups in Organic Synthesis", 2nd Ed., Greene, T. W. and related publications.

EXAMPLE 1

2-{4-[(4-Chlorophenyl)methyl]pipierazinyl}-1-(3-methylindolinyl)ethan-1-one

Part A: 3-Methylindoline

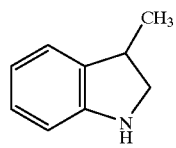

Hydrochloric acid (10.5 N, 6 mL) is added dropwise to a stirred mixture of 3-methylindole (3.93 g, 30 mmol) and trimethylamine-borane (8.75 g, 120 mmol) in room temperature dioxane (30 mL). The mixture is then heated at reflux for about 30 min. After cooling to room temperature, 6 N hydrochloric acid (24 mL) is carefully added and the mixture is refluxed for 15 min. Most of the dioxane is then removed under reduced pressure, and the residue is diluted with water (200 mL). Some insoluble material is extracted with ether, and the aqueous solution is basified with 30% aqueous sodium hydroxide to pH ~10. The oily product is extracted with ether, the extracts are washed with water and brine, dried over anhydrous MgSO$_4$, filtered and evaporated under reduced pressure to provide the product as a light yellow oil (3.75 g, 94% yield). $^1$HNMR (CDCl$_3$) δ7.08–6.69 (m, 4H), 3.75–3.70 (m, 1H), 3.39–3.37 (m, 1H), 3.14–3.10 (m, 1H), 1.33 (d, J=7.2 Hz, 4H; LC-MS (APCI, m/z) 134 (M+1)$^+$.

Part B: 2-Chloro-1-(3-methylindolinyl)ethan-1-one

Chloroacetyl chloride (3 mL, 37.5 mmol) is added dropwise to triethylamine (5 mL, 36 mmol) and 3-methylindoline (4 g, 30 mmol) in 0° C. chloroform (60 mL). The cooling bath is then removed, and after about two hours, the reaction mixture is poured into cold water, and extracted several times with dichloromethane. The combined dichloromethane extracts are washed with brine, dried over anhydrous magnesium sulfate, and filtered. The solvent is removed under reduced pressure, and the residue is crystallized from ether-hexanes to provide the product as a colorless solid (5.5 g, 87% yield). mp 78–79° C.; $^1$HNMR (CDCl$_3$) δ8.19 (d, J=7.8 Hz, 1H), 7.26–7.07 (m, 3H), 4.32 (t, J=6.8 Hz, 1H), 4.16 (s, 2H), 3.72–3.66 (m, 1H), 3.59–3.51 (m, 1H), 1.38 (d, J=6.9 Hz, 3H); LC-MS (APCI, m/z) 210 (M+1)$^+$.

Part C: 2-{4-[(4-Chlorophenyl)methyl]piperazinyl)}-1-(3-methylindolinyl)ethan-1-one

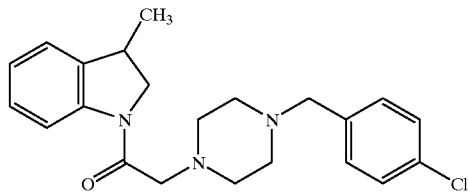

Potassium carbonate (206 mg, 1.5 mmol) and [(4-chlorophenyl)methyl]piperazine (210 mg, 1 mmol) are added to a solution of 2-chloro-1-(3-methylindolinyl)ethan-1-one (210 mg, 1 mmol) in acetonitrile (12 mL). After refluxing for about 3 h, the reaction mixture is filtered through silica gel, and concentrated. The residue is crystallized from ethyl acetate and hexanes to provide the product as a colorless solid. mp 101–103° C.; $^1$HNMR (CDCl$_3$) δ8.20 (d, J=7.8 Hz, 1H) 7.29–7.15 (m, 6H), 7.06–7.01 (m, 1H), 4.31 (t, J=6.9 Hz, 1H), 3.70–3.65 (m, 1H), 3.49 (m, 1H), 3.46 (s, 2H), 3.24 (s, 2H), 2.61 (m, 4H), 2.49 (m, 4H), 1.34 (d, J=7.5 Hz, 3H); LC-MS (APCI, m/z) 384 (M+1)$^+$.

Anal. Calcd for C$_{22}$H$_{26}$N$_3$ClO: C, 68.83; H, 6.83; N, 10.95. Found: C, 69.18; H, 6.66; N, 10.86.

EXAMPLE 2

1-((2R,3R)-2,3-Dimethylindolinyl)-2-{4-[(4-Chlorophenyl)methyl]piperazinyl}ethan-1-one, and 1-((2S,3S)-2,3-Dimethylindolinyl)-2-{4-[(4-Chlorophenyl)methyl]piperazinyl}ethan-1-one Part A: cis- and trans-2,3-Dimethylindolines

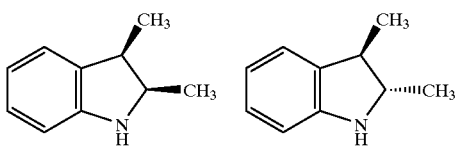

These two indolines are prepared starting from 2,3-dimethylindole according to a literature procedure. (Synthesis, 508, (Berger, 1974)).

Part B: 2-Chloro-1-(cis-2,3-dimethylindolinyl)ethan-1-one

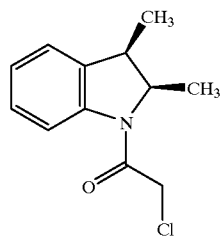

The title compound is prepared by the procedure as described in Example 1 (part B) to provide a colorless solid in 75% yield. mp 83–84° C.; $^1$HNMR (CDCl$_3$) δ8.17 (m, 1H), 7.28–7.08 (m, 7H), 4.24 (m, 1H), 4.18 (s, 2H), 2.90 (m, 1H), 1.32 (d, J=6.3 Hz, 3H), 1.25 (d, J=6.9 Hz, 3H); LC-MS (APCI, m/z) 224 (M+1)$^+$.

Part C: 1-((2R,3R)-2,3-Dimethylindolinyl)-2-{4-[(4-Chlorophenyl)methyl]piperazinyl}ethan-1-one and 1-((2S,3S)-2,3-Dimethylindolinyl)-2-{4-[(4-Chlorophenyl)methyl] piperazinyl}ethan-1-one

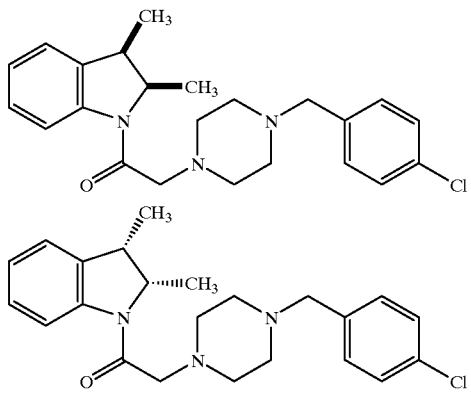

These two compounds are prepared from 2-chloro-1-(cis-2,3-dimethylindolinyl)ethan-1-one and [(4-chlorophenyl)methyl]piperazine using the procedure described in Example 1 (Part C). The enantiomers are separated by chiral preparative chromatography to provide each enantiomer as a colorless syrup in 92% overall yield. These two isomers have the same physical data except for the direction of their optical rotation as measured on a polarimeter. (2R,3R)-Isomer: [α]$_D$ +7.0°(C=0.4, CHCl$_3$); $^1$HNMR (CDCl$_3$) δ8.17 (m, 1H), 7.30–7.18 (m, 6H), 7.08–7.02 (m, 1H), 4.42 (m, 1H), 3.47 (s, 2H), 3.43 (m, 1H), 2.85 (m, 1H), 2.65 (m, 4H), 2.51 (m, 4H), 1.26 (d, J=6.3 Hz, 3H), 1.21 (d, J=7.2 Hz, 3H); LC-MS (APCI, m/z) 398 (M+1)$^+$. A portion of the product is converted to the dihydrochloride salt, mp 247–248° C. Anal. Calcd for C$_{23}$H$_{28}$N$_3$ClO.2HCl: C, 58.67; H, 6.42; N, 8.92. Found: C, 58.36; H, 6.26; N, 8.69.

EXAMPLE 3

Methyl (2S)-1-(2-{4-[(4-chlorophenyl)methyl]-piperazinyl}indoline-2-carboxylate

Part A: Methyl (2S)-1-(2-chloroacetyl)indoline-2-carboxylate

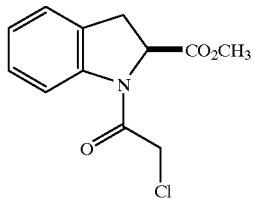

The title compound is prepared starting from methyl (2S)-1-(2-chloroacetyl)indoline-2-carboxylate monohydrate (J. Org. Chem. 62, Bertini Gross, 7679 (1997)) and chloroacetyl chloride by the procedure described in Example 1 (step B, 3 eq. triethylamine is used) to provide the product as a colorless oil in 89% yield. $^1$HNMR (CDCl$_3$) δ7.29–7.06 (m, 4H), 5.16 (m, 1H), 4.12 (s, 2H), 3.77 (s, 3H), 3.64 (m, 1H), 3.41–3.35 (m, 1H); LC-MS (APCI, m/z) 254 (M+1)$^+$.

Part B: Methyl (2S)-1-(2-{4-[(4-chlorophenyl)methyl] piperazinyl}indoline-2-carboxylate

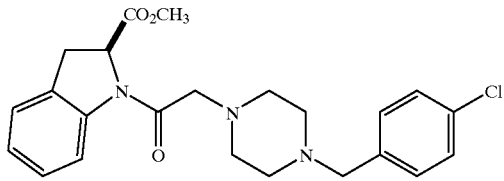

The title compound is prepared starting from methyl (2S)-1-(2-chloroacetyl)indoline-2-carboxylate and [(4-chlorophenyl)methyl]piperazine by the procedure described in Example 1 (Part C), and purified by crystallization from ethyl acetate and hexanes to provide the product as a colorless solid in 82% yield. mp 125–126° C.; $^1$HNMR (CDCl$_3$) δ8.20–8.18 (m, 1H), 7.29–7.16 (m, 6H), 7.06–7.01 (m, 1H), 5.35–5.31 (m, 1H), 3.71 (s, 3H), 3.59–3.54 (m, 1H), 3.46 (s, 2H), 3.22 (s, 2H), 3.17 (m, 1H), 2.53 (m, 4H), 2.43 (m, 4H); LC-MS (APCI, m/z) 428 (M+1)$^+$. Anal. Calcd for C$_{23}$H$_{26}$N$_3$ClO$_3$: C, 64.55; H, 6.12; N, 9.82. Found: C, 64.62; H, 6.36; N, 9.60.

EXAMPLE 4

(2S)-1-(2-{4-[(4-Chlorophenyl)methyl]piperazinyl}-acetyl) indoline-2-carboxylic acid

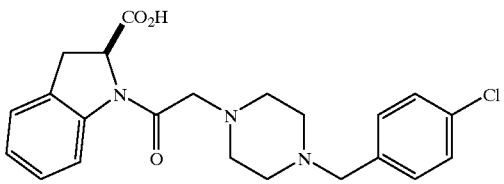

Lithium hydroxide monohydrate (160 mg, 4 mmol) is added to a solution of methyl (2S)-1-(2-{4-[(4-chlorophenyl)methyl]piperazinyl}indoline-2-carboxylate (1 g, 2.34 mmol) in methanol (12 mL) and water (4 mL). After stirring overnight at room temperature, the pH is adjusted to ~6 with 1 N hydrochloric acid. After removal of the methanol under reduced pressure, the residue is extracted several times with ethyl acetate. The combined ethyl acetate extracts are washed with brine, dried over anhydrous magnesium sulfate, and filtered. The solvent is removed under reduced pressure, and the residue is crystallized from chloroform-ether to provide the product as a colorless solid in 75% yield. mp 219–221° C.; $^1$HNMR (DMSO-d$_6$) δ6 7.98 (d, J=8.0 Hz, 1H), 7.49–7.42 (m, 4H), 7.23 (d, J=6.8 Hz, 1H), 7.16 (t, J=7.6 Hz, 1H), 7.01 (t, J=7.6 Hz, 1H), 5.15 (d, J=8.0 Hz, 1H), 3.90 (s, 2H), 3.55–3.49 (m, 2H), 3.22–3.10 (m, 2H), 2.77 (m, 4H), 2.64 (m, 4H); LC-MS (APCI, m/z) 414 (M+1)$^+$, 412 (M−1)$^-$. Anal. Calcd for C$_{22}$H$_{24}$N$_3$ClO$_3$.1.5HCl.0.25H$_2$O: C, 55.85; H, 5.54; N, 8.88. Found: C, 55.88; H, 5.58; N, 8.91.

EXAMPLE 5

[(2S)-1-(2-{4[(4-Chlorophenyl)methyl] piperazinyl}acetyl)-indoline2-yl]-N-benzylcarboxamide

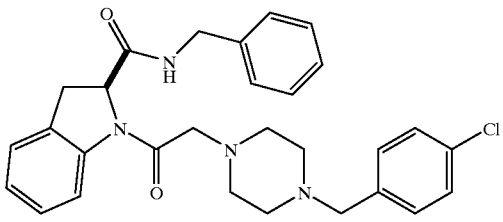

Benzylamine (32 mg, 0.3 mmol) and triethylamine (0.042 mL, 0.3 mmol) are added to a room temperature solution of (2S)-1-(2-{4-[(4-chlorophenyl)methyl]piperazinyl}acetyl) indoline-2-carboxylic acid (124 mg, 0.3 mmol) in anhydrous N,N-dimethylformamide (3 mL). After stirring for 5 min, 1-(3-dimethylaminopropyl)-3-ethylcarbodiimide hydrochloride (58 mg, 0.3 mmol) is added and the reaction mixture is stirred overnight. The reaction mixture is then poured into saturated sodium bicarbonate, and extracted several times with ethyl acetate. The combined ethyl acetate extracts are washed with brine, dried over anhydrous magnesium sulfate, and filtered. The solvent is removed under reduced pressure, and the residue is purified by silica gel chromatography with chloroform and methanol as eluents to provide the product as a colorless solid in 70% yield. mp 154–155° C.; $^1$HNMR (CDCl$_3$) δ8.13 (m, 1H), 7.29–7.21

(m, 10H), 7.09 (t, J=7.6 Hz, 2H), 6.36 (br s, 1H), 5.30 (d, J=6.0 Hz, 1H), 4.42–4.36 (m, 2H), 3.62 (m, 1H), 3.45 (s, 2H), 3.28 (m, 3H), 2.55 (m, 4H), 2.44 (m, 4H); LC-MS (APCI, m/z) 503 (M+1)$^+$, 501 (M−1)$^-$. Anal. Calcd for $C_{29}H_{31}N_4ClO_2 \cdot 1\,H_2O$: C, 66.85; H, 6.38; N, 10.75. Found: C, 66.72; H, 6.09; N, 11.05.

EXAMPLE 6

1-[(2S)-2-(Hydroxymethyl)indolinyl]-2-{4-[(4-chlorophenyl)methyl]piperazinyl}ethan-1-one Part A: Ethyl 2-{4-[(4-chlorophenyl)methyl]piperazinyl}acetate

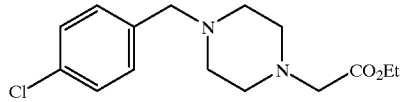

Potassium carbonate (3.12 g, 22.5 mmol), 1-[(4-chlorophenyl)methyl]piperazine (3.15 g, 15 mmol) and ethyl chloroacetate (1.84 g, 15 mmol) are refluxed in acetonitrile (100 mL) for about 3 h. The room temperature reaction mixture is filtered through silica gel, concentrated under reduced pressure, and then dried in vacuo to provide the product as a light yellow syrup (4.3 g, 97% yield). $^1$HNMR (CDCl$_3$) δ7.29–7.23 (m, 4H), 4.18 (q, J=7.2 Hz, 2H), 3.47 (s, 2H), 3.20 (s, 2H), 2.60 (br s, 4H), 2.52 (br s, 4H), 1.26 (td, J=7.2, 0.6 Hz, 3H); LC-MS (APCI, m/z) 297 (M+1)$^+$.

Part B: 2-{4-[(4-chlorophenyl)methyl]piperazinyl}acetic acid

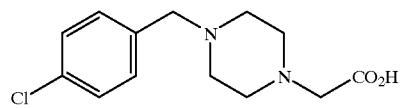

The title compound is prepared starting from ethyl 2-{4-[(4-chlorophenyl)methyl]piperazinyl}acetate by the procedure described in Example 4 to provide the product as a white solid in 80% yield. mp 190–192° C.; $^1$HNMR (CD$_3$OD) δ7.50–7.46 ( m, 4H), 4.15 (s, 2H), 3.56 (s, 2H), 3.15 (br s, 4H), 3.09 (br s, 4H); LC-MS (APCI, m/z) 269 (M+1)$^+$, 267 (M−1).

Part C: 1-[(2S)-2-(hydroxymethyl)indolinyl]-2-{4-[(4-chlorophenyl)methyl]piperazinyl}ethan-1-one

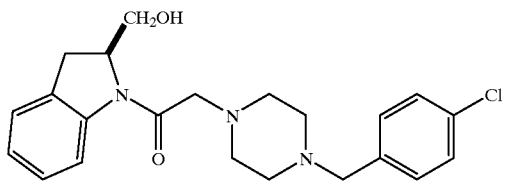

The title compound is prepared from ((2S)-indolin-2-yl) methan-1-ol (J. Org. Chem. 62, Bertini Gross, 7679 (1997)) and chloroacetyl chloride by the procedure described in Example 5. The sample is purified by silica gel chromatography to provide the product as a colorless oil. $^1$HNMR (CDCl$_3$) δ8.07 (m, 1H), 7.29–7.18 (m, 6H), 7.08–7.02 (m, 1H), 4.03 (br s, 1H), 3.66 (m, 2H), 3.58 (s, 2H), 3.47 (s, 2H), 3.38–3.31 (m, 2H), 3.18–3.07 (m, 1H); LC-MS (APCI, m/z) 400 (M+1)$^+$. A portion of the product is converted to the dihydrochloride salt. Anal. Calcd for $C_{22}H_{26}N_3ClO_2 \cdot 2HCl \cdot 1.25\,H_2O$: C, 53.34; H, 6.21; N, 8.48. Found: C, 53.36; H, 6.04; N, 8.77.

EXAMPLE 7

1-((2S)-2-Vinylindolinyl)-2-{4-[(4-chlorophenyl)methyl]piperazinyl}ethan-1-one

Part A: tert-Butyl (2S)-2-formylindolinecarboxylate

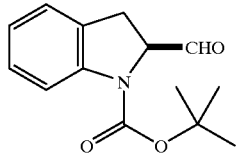

A solution of dimethyl sulfoxide (2.83 mL, 40 mmol) in anhydrous dichloromethane (5 mL) is added to a −60° C. solution of oxalyl chloride (10 mL, 2.0 M in dichloromethane, 20 mmol) in anhydrous dichloromethane (20 mL). After 5 min, tert-butyl (2S)-2-(hydroxymethyl) indolinecarboxylate (J. Org. Chem. 62, Bertini Gross, 7679 (1997)) (2.49 g, 10 mmol) in anhydrous dichloromethane (10 mL) is added dropwise maintaining the temperature at −50~−60° C. After another 3 h, triethylamine (8.2 mL) is added dropwise to the reaction mixture while keeping the temperature at or below −50° C. After stirring at room temperature for 30 min, water is added, and the reaction mixture is stirred for an additional 30 min. The reaction mixture is extracted several times with ethyl acetate, and the combined ethyl acetate extracts are washed with brine, dried over anhydrous magnesium sulfate, and filtered. The solvent is removed under reduced pressure, and the residue is purified by silica gel chromatography with ethyl acetate and hexanes as eluents to provide the product as a colorless oil (2.1 g, 84% yield). $^1$HNMR (CDCl$_3$) δ9.66 (s, 1H), 7.27–7.22 (m, 2H), 7.16–7.14 (m 1H), 7.01–6.96 (m, 1H), 4.77 (m, 1H), 3.40 (m, 1H), 3.17–3.13 (m, 1H), 1.53 (s, 9H).

Part B: tert-Butyl (2S)-2-vinylindolinecarboxylate

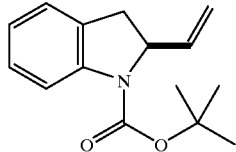

n-Butyl lithium (2.2 mL, 2.5 M in hexane, 5.5 mmol) is added dropwise to a suspension of methyltriphenylphosphonium bromide (2.14 g, 6 mmol) in 0° C. anhydrous tetrahydrofuran (16 mL). The cooling bath is then removed and the yellow solution is stirred at room temperature for 30 min. The solution is cooled to 0° C. again and tert-butyl (2S)-2-formylindolinecarboxylate (1.24 g, 5 mmol) is added dropwise over 10 min. After continued stirring for additional 30 min, the mixture is poured into ice-water, and extracted several times with ether. The extracts are washed with brine, dried over anhydrous magnesium sulfate, and filtered. The solvent is removed under reduced pressure, and the residue is purified by silica gel chromatography with ethyl acetate and hexanes as eluents to provide the product as a colorless oil (1.9 g, 89% yield). $^1$HNMR (CDCl$_3$) δ1.72 (m, 1H), 7.20–7.11 (m, 2H), 6.96–6.91 (m 1H), 5.90–5.78 (m, 1H), 5.15 (d, J=17.1 Hz, 1H), 5.07 (d, J=10.2 Hz, 1H), 4.87 (m, 1H), 3.45–3.37 (m, 1H), 2.79 (dd, J=16.2, 2.7 Hz, 1H), 1.54 (s, 9H).

Part C: (2S)-2-Vinylindoline

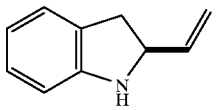

Trifluoroacetic acid (2 mL) is added dropwise to a solution of tert-butyl (2S)-2-vinylindolinecarboxylate (536 mg, 2.2 mmol) in anhydrous, 0° C. dichloromethane (4 mL). After stirring at room temperature overnight, the solvent and excess TFA are removed under reduced pressure to provide a syrup which is used in the next step without further purification. LC-MS (APCI, m/z) 146 (M+1)$^+$.

Part D: 1-((2S)-2-Vinylindolinyl)-2-chloroethan-1-one

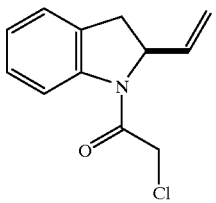

The title compound is prepared from (2S)-2-vinylindoline and chloroacetyl chloride by the procedure described in Example 1 (step B, 5 eq. triethylamine is used) to provide the product as a colorless oil in 82% yield (two steps). $^1$HNMR (CDCl$_3$) δ8.21 (m, 1H), 7.27–7.18 (m, 2H), 7.11–7.06 (m, 1H), 5.96–5.85 (m, 1H), 5.126–5.17 (m, 2H), 5.01 (m, 1H), 4.28 (d, J=12.9 Hz, 1H), 4.17–4.09 (m, 1H), 3.62–3.54 (m, 1H), 2.89 (d, J=15.6 Hz, 1H); LC-MS (APCI, m/z) 222 (M+1)$^+$.

Part E: 1-((2S)-2-Vinylindolinyl)-2-{4-[(4-chlorophenyl)methyl]piperazinyl}ethan-1-one

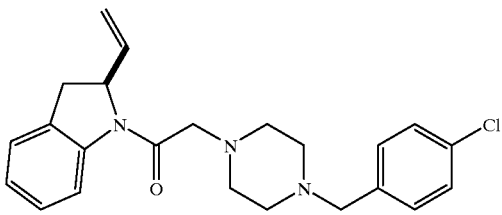

The title compound is prepared from 1-((2S)-2-Vinylindolinyl)-2-chloroethan-1-one and [(4-chlorophenyl)methyl]piperazine by the procedure described in Example 1 (Part C), and purified by silica gel chromatography with chloroform and methanol as eluents to provide the product as a colorless syrup in 90% yield. $^1$HNMR (CDCl$_3$) δ8.23 (m, 2H), 7.26–7.15 (m, 6H), 7.05–7.0 (m, 1H), 5.90–5.79 (m, 1H), 5.23 (m, 1H), 5.15–5.09 (m, 2H), 3.48–3.40 (m, 4H), 3.24–3.12 (m, 1H), 2.81 (d, J=15.9 Hz, 1H), 2.61 (m, 4H), 2.50 (m, 4H); LC-MS (APCI, m/z) 396 (M+1)$^+$. A portion of the product can be converted to the dihydrochloride salt, mp 229–230° C.; Anal. Calcd for C$_{23}$H$_{26}$N$_3$ClO.2 HCl.1 H$_2$O: C, 56.74; H, 6.21; N, 8.63. Found: C, 56.79; H, 5.97; N, 8.44.

EXAMPLE 8

1-((2S)-2-(Fluoromethylindolinyl)-2-{4-[(4-chlorophenyl)methyl]piperazinyl}ethan-1-one Part A: Methyl (2S)-1-benzylindoline-2-carboxylate

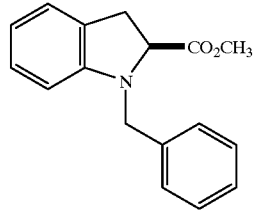

Potassium carbonate (1.4 g, 10 mmol), benzyl bromide (0.62 mL, 5.1 mmol) and methyl (2S)-1-(2-chloroacetyl) indoline-2-carboxylate monohydrate (1.07 g, 5 mmol) are refluxed in acetonitrile (30 mL) for about 8 h. The room temperature reaction mixture is filtered through silica gel and the filtrate is concentrated under reduced pressure. The residue is then dried in vacuo to provide the product as a light yellow syrup (2.64 g, 99% yield). [α]$_D$ +25.3° (c=1.8, CHCl$_3$); $^1$HNMR (CDCl$_3$) δ7.36–7.26 ( m, 5H), 7.07–7.02 (m, 2H), 6.71–6.67 (m, 1H), 6.46 (d, J=7.8 Hz, 1H), 4.52 (d, J=15.3 Hz, 1H), 4.32 (d, J=15.3 Hz, 1H), 4.25 (m, 1H), 3.67 (s, 3H), 3.39 (dd, J=15.9, 9.9 Hz, 1H), 3.19 (dd, J=15.9, 9.9 Hz, 1H); LC-MS (APCI, m/z) 268 (M+1)$^+$.

Part B: [(2S)-1-benzylindolin-2-yl]methan-1-ol

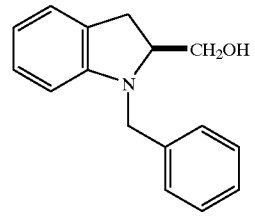

Lithium aluminum hydride (20 mL, 1 M in anhydrous tetrahydrofuran, 4 mmol) is added dropwise to a 0° C. the solution of methyl (2S)-1-benzylindoline-2-carboxylate (5.35 g, 20 mmol) in anhydrous tetrahydrofuran (60 mL). The cooling bath is then removed and the reaction mixture is stirred at room temperature for about 5 h. Freshly prepared saturated sodium sulfate solution is added to quench the reaction. The reaction mixture is filtered through silica gel, dried over anhydrous sodium sulfate, and filtered. The solvent is removed under reduced pressure, and dried in vacuo to provide the product as a light yellow oil (4.56 g, 95% yield). [α]$_D$ −22° (c=1.9, CHCl$_3$); $^1$HNMR (CDCl$_3$) δ7.38–7.25 (m, 5H), 7.11–7.02 (m, 2H), 6.74–6.69 (m, 1H), 6.50 (d, J=7.8 Hz, 1H), 4.36 (s, 2H), 3.86–3.77 (m, 2H), 3.14–3.09 (m, 2H), 1.71–1.59 (m, 2H); LC-MS (APCI, m/z) 240 (M+1)$^+$.

Part C: [(2S)-2-(Fluoromethyl)]-1-benzylindoline

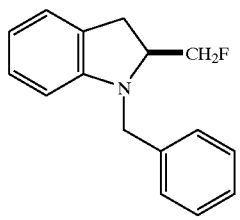

Diethylaminosulfur trifluoride (DAST, 2.02 mL, 15 mmol) is added dropwise to a −70° C. solution of [(2S)-1-benzylindolin-2-yl]methan-1-ol (3.59 g, 15 mmol) in anhydrous dichloromethane (60 mL). The reaction mixture is stirred at −70° C. for 2 h, and then at room temperature for about 2 h. The reaction is quenched by addition of sodium carbonate solution, and the reaction mixture is extracted several times with dichloromethane. The combined dichloromethane extracts were washed with brine, dried over anhydrous magnesium sulfate, and filtered. The solvent is removed under reduced pressure, and the residue is purified by silica gel chromatography with ethyl acetate and hexanes as eluents to provide the product as a colorless oil (3.36 g, 94% yield). $[\alpha]_D$ +6.0° (c=1.1, CHCl$_3$); 1HNMR (CDCl$_3$) $\delta$7.36–7.25 (m, 5H), 7.06–7.01 (m, 2H), 6.69–6.64 (m, 1H), 6.57 (d, J=6.9 Hz, 1H), 5.27–5.24, 5.11–5.06 (m, 1H), 4.53 (s, 2H), 3.59–3.49 (m, 2H), 3.19–3.08 (m, 2H); LC-MS (APCI, m/z) 241.9 (M+1)$^+$.

Part D: (2S)-2-Fluoromethylindoline

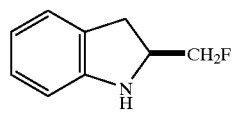

A mixture of [(2S)-2-(Fluoromethyl)]-1-benzylindoline (2.34 g, 9.7 mmol) and 10% Pd/C (Degussa type E101 NE/W, 2 g) in anhydrous methanol (80 mL) is hydrogenated at room temperature under 45 psi pressure until the uptake of hydrogen ceases (approximately 24 h). The reaction mixture is filtered through celite and concentrated under reduced pressure at temperatures below 30° C. The residue is purified by silica gel chromatography to provide the product as a syrup (1.12 g, 76% yield). $[\alpha]_D$ +19.50°(c=1.2, CHCl$_3$); $^1$HNMR (CDCl$_3$) $\delta$7.04–6.98 (m, 2H), 7.71–6.66 (m, 1H), 6.55 (d, J=6.9 Hz, 1H), 5.21–5.18, 5.06–5.0 (m, 1H), 3.78 (br s, 1H), 3.50–3.42 (m, 2H), 3.14–3.03 (m, 2H); LC-MS (APCI, m/z) 151.9 (M+1)$^+$.

Part E: 1-((2S)-2-Fluoromethylindolinyl)-2-chloroethan-1-one

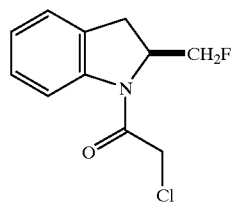

The title compound is prepared from (2S)-2-fluoromethylindoline and chloroacetyl chloride by the procedure described in Example 1 (step B, 1.2 eq. triethylamine is used), and purified by silica gel chromatography to provide the product as a colorless solid in 88% yield. mp 60–61° C.; $[\alpha]_D$ −32°(c=0.5, CHCl$_3$); $^1$HNMR (CDCl$_3$) $\delta$7.31–7.25 (m, 4H), 5.39–5.33, 5.22–5.16 (m, 1H), 4.24 (s, 2H), 4.12–4.05 (m, 2H), 3.12–3.0 (m, 2H); LC-MS (APCI, m/z) 228 (M+1)$^+$.

Part F: 1-((2S)-2-(Fluoromethylindolinyl)-2-{4-[(4-chlorophenyl)methyl]piperazinyl}ethan-1-one

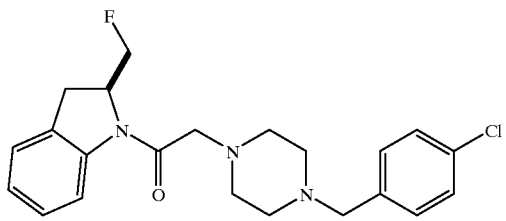

The title compound is prepared from 1-((2S)-2-fluoromethylindolinyl)-2-chloroethan-1-one and [(4-chlorophenyl)methyl]piperazine by the procedure described in Example 1 (Part C), and purified by silica gel chromatography with chloroform and methanol as eluents to provide the product as a colorless syrup in 92% yield. $[\alpha]_D$ −7.8° (c=1.2, CHCl$_3$); $^1$HNMR (CDCl$_3$) $\delta$7.42 (m, 1H), 7.29–7.13 (m, 7H), 5.31–5.27, 5.15–5.10 (m, 1H), 4.22–3.92 (m, 2H), 3.43 (s, 2H), 3.33–3.24 (m, 2H), 3.06 (m, 1H), 2.99 (m, 1H), 2.52 (m, 4H), 2.42 (m, 4H); LC-MS (APCI, m/z) 402 (M+1)$^+$. A portion of the product is converted to the dihydrochloride salt, mp 219–220° C.

EXAMPLE 9

1-((2S)-2-(Difluoromethylindolinyl)-2-{4-[(4-chlorophenyl)methyl]piperazinyl}ethan-1-one Part A: (2S)-Indoline-2-carbaldehyde

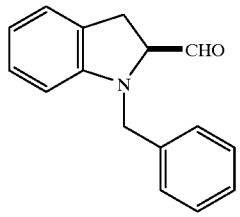

The title compound is prepared from [(2S)-1-benzylindolin-2-yl]methan-1-ol by the procedure described in Example 7 (Part A), and purified by silica gel chromatography with ethyl acetate and hexanes as eluents to provide the product as a colorless syrup in 82% yield. $[\alpha]_D$ +36° (c=2.2, CHCl$_3$); $^1$HNMR (CDCl$_3$) $\delta$9.49 (d, J=7.2 Hz, 1H), 7.35–7.31 (m, 5H), 7.14–7.09 (m, 2H), 6.78–6.73 (m, 1H), 6.59 (d, J=7.8 Hz, 1H), 4.46 (d, J=15.0 Hz, 1H), 4.28 (d, J=15.3 Hz, 1H), 4.12–4.04 (m, 1H), 3.33–3.24 (m, 1H), 3.13–3.05 (m, 1H); LC-MS (APCI, m/z) 238 (M+1)$^+$.

Part B: [(2S)-2-(Difluoromethyl)]-1-benzylindoline

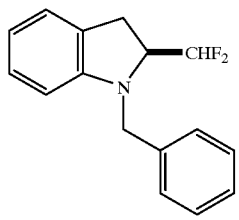

The title compound is prepared from (2S)-indoline-2-carbaldehyde by the procedure described in Example 8 (Part C), and purified by silica gel chromatography with ethyl ether and hexanes as eluents to provide the product as a colorless syrup in 77% yield. $^1$HNMR (CDCl$_3$) δ7.32–7.26 (m, 5H), 7.10–7.03 (m, 2H), 6.72 (t, J=7.5 Hz, 2H), 6.46 (d, J=7.8 Hz, 1H), 5.94, 5.76, 5.57 (d, J=5.4 Hz, 1H), 4.56 (d, J=16.2 Hz, 1H), 4.36 (d, J=15.9 Hz, 1H), 3.34–3.25 (m, 1H), 3.10–3.02 (m, 1H); $^{19}$FNMR (CDCl$_3$) δ44.3–37.0 (m, 2F); LC-MS (APCI, m/z) 260 (M+1)$^+$.

Part C: (2S)-2-Difluoromethylindoline

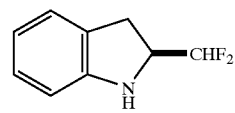

The title compound is prepared from (2S)-indoline-2-carbaldehyde by the procedure described in Example 8 (Part D), and purified by silica gel chromatography with ethyl ether and hexanes as eluents to provide the product as a colorless syrup in 78% yield.

Part D: 1-((2S)-2-Difluoromethylindolinyl)-2-chloroethan-1-one

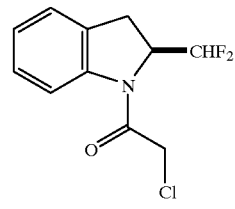

The compound is prepared from (2S)-2-difluoromethylindoline and chloroacetyl chloride by the procedure described in Example 1 (step B, 1.2 eq. triethylamine is used), and purified by silica gel chromatography to provide the product as a colorless solid in 88% yield.

Part E: 1-((2S)-2-(Difluoromethylindolinyl))-2-{4-[(4-chlorophenyl)methyl]piperazinyl}ethan-1-one

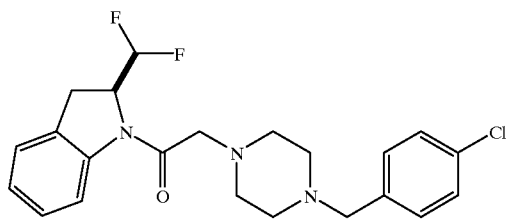

The title compound is prepared from 1-((2S)-2-Fluoromethylindolinyl)-2-chloroethan-1-one and [(4-chlorophenyl)methyl]piperazine by the procedure described in Example 1 (Part C), and purified by silica gel chromatography with chloroform and methanol as eluents to provide the product as a colorless syrup in 92% yield.

EXAMPLE 10

The following compounds are prepared essentially according to the procedures set forth above in Schemes 1–6 and the above examples.

(a) 2-{4-[(4-methylphenyl)methyl]piperazinyl}-1-(3-methylindolinyl)ethan-1-one,
(b) 2-{4-[(4-fluorophenyl)methyl]piperazinyl}-1-(3-methylindolinyl)ethan-1-one,
(c) 2-{4-[(4-ethylphenyl)methyl]piperazinyl}-1-(3-methylindolinyl)ethan-1-one,
(d) 2-{4-[(4-isopropylphenyl)methyl]piperazinyl}-1-(3-methylindolinyl)ethan-1-one,
(e) 2-{4-[(4-trifluoromethylphenyl)methyl]piperazinyl}-1-(3-methylindolinyl)ethan-1-one,
(f) 2-{4-[(4-methoxyphenyl)methyl]piperazinyl}-1-(3-methylindolinyl)ethan-1-one,
(g) 1-(2,3-cis-dimethylindolinyl)-2-{4-[(4-methylphenyl)methyl]piperazinyl}ethan-1-one,
(h) 1-(2,3-cis-dimethylindolinyl)-2-{4-[(4-methoxyphenyl)methyl]piperazinyl}ethan-1-one,
(i) 1-(2,3-cis-dimethylindolinyl)-2-{4-[(3-chloro-6-methoxyphenyl)methyl]piperazinyl}ethan-1-one,
(j) 1-(2,3-cis-dimethylindolinyl)-2-{4-[(4-ethylphenyl)methyl]piperazinyl}ethan-1-one,
(k) 1-(2,3-trans-dimethylindolinyl)-2-{4-[(4-chlorophenyl)methyl]piperazinyl}ethan-1-one,
(l) 1-(2,3-trans-dimethylindolinyl)-2-{4-[(4-methylphenyl)methyl]piperazinyl}ethan-1-one,
(m) 1-[(4b,8a-cis-5,6,7,8,9,4b,8a-heptahydro-4aH-carbazol-9-yl) ethyl]-2-{4-[(4-chlorophenyl)methyl]piperazinyl}ethan-1-one,
(n) 1-[(4b,8a-cis-5,6,7,8,9,4b,8a-heptahydro-4aH-carbazol-9-yl) ethyl]-2-{4-[(4-methylphenyl)methyl]piperazinyl}ethan-1-one (Table 1, lo),
(o) 1-[(4b,8a-cis-5,6,7,8,9,4b,8a-heptahydro-4aH-carbazol-9-yl)ethyl]-2-{4-[(4-isopropylphenyl)methyl]piperazinyl}ethan-1-one,
(p) 1-[(4b,8a-cis-5,6,7,8,9,4b,8a-heptahydro-4aH-carbazol-9-yl) ethyl]-2-{4-[(4-fluorophenyl)methyl]piperazinyl}ethan-1-one,
(q) methyl (2S)-1-(2-{4-[(4-methylphenyl)methyl]piperazinyl}indoline-2-carboxylate,
(r) methyl (2R)-1-(2-{4-[(4-chlorophenyl)methyl]piperazinyl}indoline-2-carboxylate,
(s) methyl (2R)-1-(2-{4-[(4-methylphenyl)methyl]piperazinyl}indoline-2-carboxylate,
(t) (2S)-1-(2-{4-[(4-methylphenyl)methyl]piperazinyl}acetyl)indoline-2-carboxylic acid,
(u) (2R)-1-(2-{4-[(4-chlorophenyl)methyl]piperazinyl}acetyl)indoline-2-carboxylic acid,
(v) [(2S)-1-(2-{4-[(4-methylphenyl)methyl]piperazinyl}acetyl)indoline-2-yl]-N-benzylcarboxamide,
(w) [(2S)-1-(2-{4-[(4-chlorophenyl)methyl]piperazinyl}acetyl)indoline-2-yl]-N-carboxamide,
(x) [(2S)-1-(2-{4-[(4-methylphenyl)methyl]piperazinyl}acetyl)indoline-2-yl]-N,N-dimethylcarboxamide,
(y) 1-[(2S)-2-(hydroxymethyl)indolinyl]-2-{4-[(4-methylphenyl)methyl]piperazinyl}ethan-1-one,
(z) 1-[(2S)-2-(methoxymethyl)indolinyl]-2-{4-[(4-chlorophenyl)methyl]piperazinyl}ethan-1-one (Table 1, 1k), (aa) 1-((2S)-2-vinylindolinyl)-2-{4-[(4-methylphenyl)methyl]piperazinyl}ethan-1-one,
(bb) 1-((2S)-2-(fluoromethylindolinyl)-2-{4-[(4-methylphenyl)methyl]piperazinyl}ethan-1-one,
(cc) 1-((2S)-2-(difluoromethylindolinyl)-2-{4-[(4-chlorophenyl)methyl]piperazinyl}ethan-1-one.

EXAMPLE 11
Determination of $D_2$ and $D_4$ Receptor Binding Activity

The following assay is used for determining the binding affinity of compounds to dopamine $D_4$ and $D_2$ receptors.

Pellets of Chinese hamster ovary (CHO) cells containing recombinantly expressing primate $D_2$, human $D_4$ or human 1 receptors are used for the assays. The sample is homogenized in 100 volumes (w/vol) of 0.05 M Tris HCl buffer containing 120 mM NaCl, 5 mM $MgCl_2$ and 1 mM EDTA at 4° C. and pH 7.4. The sample is then centrifuged at 30,000×g, resuspended and rehomogenized. The sample is then recentrifuged at 30,000×g, the supernatant is removed and the final tissue sample is frozen until it is needed. The tissue is resuspended 1:20 (wt/vol) in 0.05 M Tris HCl buffer containing 120 mM NaCl.

Incubations for dopaminergic binding are carried out at 25° C. and contain 0.4 ml of tissue sample, 0.1 nM $^3$H-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation volume of 1.0 ml. Nonspecific binding is defined as that binding found in the presence of 1 M spiperone; without further additions, nonspecific binding is less than 20% of total binding.

Binding characteristics for various compounds of the invention for $D_2$ and $D_4$ primate or human dopamine receptor subtypes are shown in Table 2.

TABLE 2

| Compound Number | $D_2$ $K_i$ (nM) | $D_4$ $K_i$ (nM) |
| --- | --- | --- |
| 1a | 4375 | 96 |
| 1b | 2638 | 93 |
| 1c | 185 | 2 |
| 1d | 473 | 70 |
| 1e | 128 | 22 |
| 1f | 183 | 206 |
| 1g | 1178 | 5 |
| 1j | 3207 | 10 |
| 1l | 271 | 5 |
| 1m | 1096 | 21 |
| 1o | 200 | 11 |

Preferred compounds of the invention exhibit Ki values of less than 500 nM at the dopamine $D_4$ receptor, more preferred compounds exhibit $K_i$ values of less than 100 nM and most preferred compounds of the invention exhibit $K_i$ values of less than 20 nM. Preferred compounds of the invention also exhibit greater than 20-fold selectivity for the dopamine $D_4$ receptor over the dopamine $D_2$ receptor; more preferred compounds of the invention exhibit greater than 100-fold selectivity for the dopamine $D_4$ receptor over the dopamine $D_2$ receptor.

EXAMPLE 12
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

EXAMPLE 12a

Radiolabeled compounds of the invention may be synthesized via the method shown in Scheme I using ARC-802 Indole, [2-$^{14}$C(U)], supplied by American Radiolabeled Chemicals, Inc., St. Louis, Mo., as the radioisotope precursor.

EXAMPLE 13
Use of Compounds of the Invention as Probes for Dopamine Receptors in Cultured Cells and Tissue Samples Receptor autoradiography (receptor mapping) of dopamine receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

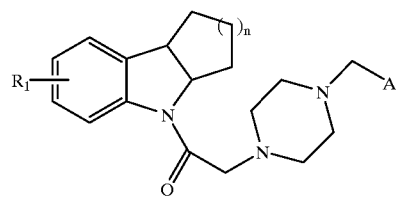

or a pharmaceutically acceptable salt thereof, wherein n is 1, 2, or 3;

A represents a phenyl group optionally substituted with up to four groups independently selected from halogen, hydroxy, amino, mono- or di($C_1$-$C_6$) hydrocarbylamino, aminosulfonyl, $C_1$-$C_6$ hydrocarbylaminosulfonyl, di($C_1$-$C_6$) hydrocarbylaminosulfonyl, cyano, nitro, cyclohydrocarbylhydrocarbyl, trifluoromethyl, $C_1$–$C_6$ hydrocarbyl, trifluoromethoxy, $C_3$–$C_6$ cyclohydrocarbyl, and $C_1$–$C_6$ alkoxy; and $R_1$ represents hydrogen, halogen, hydroxy, amino, aminosulfonyl, $C_1$–$C_6$ hydrocarbylaminosulfonyl, di($C_1$–$C_6$)hydrocarbylaminosulfonyl, cyano, nitro, trifluoromethyl, trifluoromethoxy, $C_1$–$C_6$ hydrocarbyl, cyclohydrocarbylhydrocarbyl, $C_3$–$C_7$ cyclohydrocarbyl, and $C_1$–$C_6$ alkoxy.

2. A compound according to claim 1, wherein

A represents a phenyl group optionally substituted with up to four groups independently selected from halogen, hydroxy, amino, mono- or di($C_1$–$C_6$)alkylamino, aminosulfonyl, $C_1$–$C_6$ alkylaminosulfonyl, di($C_1$–$C_6$) alkylaminosulfonyl, cyano, nitro, cycloalkylalkyl, trifluoromethyl, ($C_1$–$C_6$)alkyl, trifluoromethoxy, $C_3$–$C_6$ cycloalkyl, and $C_1$–$C_6$ alkoxy; and $R_1$ represents hydrogen, halogen, hydroxy, amino, aminosulfonyl, $C_1$–$C_6$ alkylaminosulfonyl, di($C_1$–$C_6$) alkylaminosulfonyl, cyano, nitro, trifluoromethyl, trifluoromethoxy, ($C_1$–$C_6$)alkyl, cycloalkylalkyl, $C_3$–$C_6$ cycloalkyl, and $C_1$–$C_6$ alkoxy.

3. A compound according to claim 2, wherein A is a group of the formula:

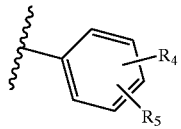

where $R_4$ and $R_5$ independently represent hydrogen, halogen, hydroxy, amino, mono- or di($C_1$–$C_6$)alkylamino, aminosulfonyl, $C_1$–$C_6$ alkylaminosulfonyl, di($C_1$–$C_6$) alkylaminosulfonyl, cyano, nitro, trifluoromethoxy, $C_1$–$C_6$ alkyl, or $C_1$–$C_6$ alkoxy.

4. A compound according to claim 3, wherein n is 1.

5. A compound according to claim 3, wherein n is 2.

6. A compound according to claim 4, wherein $R_4$ and $R_5$ independently represent hydrogen, halogen, $C_1$–$C_6$ alkoxy, or $C_1$–$C_6$ alkyl.

7. A compound according to claim 5, wherein $R_4$ and $R_5$ independently represent hydrogen, halogen, $C_1$–$C_6$ alkoxy, or $C_1$–$C_6$ alkyl.

8. A compound of the formula:

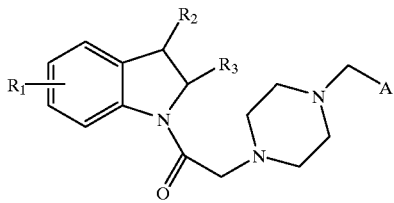

or a pharmaceutically acceptable salt thereof, wherein

A represents a phenyl group optionally substituted with up to four groups independently selected from halogen, hydroxy, amino, mono- or di($C_1$–$C_6$) hydrocarbylamino, aminosulfonyl, $C_1$–$C_6$ hydrocarbylaminosulfonyl, di($C_1$–$C_6$) hydrocarbylaminosulfonyl, cyano, nitro, cyclohydrocarbylhydrocarbyl, trifluoromethyl, $C_1$–$C_6$ hydrocarbyl, trifluoromethoxy, $C_3$–$C_6$ cyclohydrocarbyl, and $C_1$–$C_6$ alkoxy;

$R_1$ represents hydrogen, halogen, hydroxy, amino, aminosulfonyl, $C_1$–$C_6$ hydrocarbylaminosulfonyl, di($C_1$–$C_6$)hydrocarbylaminosulfonyl, cyano, nitro, trifluoromethyl, trifluoromethoxy, $C_1$–$C_6$ hydrocarbyl, cyclohydrocarbylhydrocarbyl, $C_3$–$C_7$ cyclohydrocarbyl, and $C_1$–$C_6$ alkoxy; and $R_2$ is hydrogen and $R_3$ is mono, di, or trifluoromethyl, hydroxy($C_1$–$C_3$)hydrocarbyl, $C_1$–$C_6$ alkoxy($C_1$–$C_3$) hydrocarbyl, mono or di($C_1$–$C_6$)hydrocarbylamino ($C_1$–$C_3$)hydrocarbyl, carboxamido, mono or dihydrocarbylaminocarbonyl, aminohydrocarbyl, carboxy, $C_1$–$C_6$ alkoxycarbonyl, carbamoyl, mono or di($C_1$–$C_6$)hydrocarbylcarbamoyl, aryl($C_1$–$C_6$) hydrocarbylcarbamoyl, or N,N-(aryl($C_1$–$C_6$) hydrocarbyl) (($C_1$–$C_6$)hydrocarbyl)carbamoyl; or $R_3$ is hydrogen and $R_2$ is mono, di, or trifluoromethyl, hydroxy($C_1$–$C_3$)hydrocarbyl, $C_1$–$C_6$ alkoxy($C_1$–$C_3$) hydrocarbyl, mono or di($C_1$–$C_6$)hydrocarbylamino ($C_1$–$C_3$)hydrocarbyl, carboxamido, mono or dihydrocarbylaminocarbonyl, aminohydrocarbyl, carboxy, $C_1$–$C_6$ alkoxycarbonyl, carbamoyl, mono or di($C_1$–$C_6$)hydrocarbylcarbamoyl, aryl($C_1$–$C_6$) hydrocarbylcarbamoyl, N,N-(aryl($C_1$–$C_6$)hydrocarbyl) (($C_1$–$C_6$)hydrocarbyl)carbamoyl, or alkenyl.

9. A compound according to claim 8, wherein $R_2$ is hydrogen and $R_3$ is mono, di, or trifluoromethyl, hydroxy ($C_1$–$C_3$)alkyl, $C_1$–$C_6$ alkoxy($C_1$–$C_3$)alkyl, mono or di($C_1$–$C_6$)alkylamino($C_1$–$C_3$)alkyl, aminoalkyl, carboxy, $C_1$–$C_6$ alkoxycarbonyl, carbamoyl, mono or di($C_1$–$C_6$) alkylcarbamoyl, aryl($C_1$–$C_6$)alkylcarbamoyl, N,N-(aryl ($C_1$–$C_6$)alkyl) (($C_1$–$C_6$)alkyl)carbamoyl, or alkenyl.

10. A compound according to claim 9, wherein A is a group of the formula:

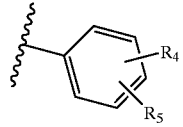

where $R_4$ and $R_5$ independently represent hydrogen, halogen, hydroxy, amino, mono- or di($C_1$–$C_6$)alkylamino, aminosulfonyl, $C_1$–$C_6$ alkylaminosulfonyl, di($C_1$–$C_6$) alkylaminosulfonyl, cyano, nitro, trifluoromethoxy, $C_1$–$C_6$ alkyl, or $C_1$–$C_6$ alkoxy.

11. A compound according to claim 10, wherein $R_4$ and $R_5$ independently represent hydrogen, halogen, $C_1$–$C_6$ alkoxy, or $C_1$–$C_6$ alkyl.

12. A compound according to claim 11, wherein $R_2$ is hydrogen and $R_3$ is hydroxy($C_1$–$C_3$)alkyl, $C_1$–$C_6$ alkoxy ($C_1$–$C_3$)alkyl, mono or di($C_1$–$C_6$)alkylamino($C_1$–$C_3$)alkyl, aminoalkyl, carboxy, or $C_1$–$C_6$ alkoxycarbonyl.

13. A compound according to claim 1, which is 1-[(4b, 8a-cis-5,6,7,8,9,4b,8a-heptahydro-4aH-carbazol-9-yl) ethyl]-2-{4-[(4-chlorophenyl)methyl]piperazinyl}ethan-1-one.

14. A compound according to claim 1, which is 1-[(4b, 8a-cis-5,6,7,8,9,4b,8a-heptahydro-4aH-carbazol-9-yl) ethyl]-2-{4-[(4-methylphenyl)methyl]piperazinyl}ethan-1-one.

15. A compound according to claim 1, which is 1-[(4b, 8a-cis-5,6,7,8,9,4b,8a-heptahydro-4aH-carbazol-9-yl) ethyl]-2-{4-[(4-ethylphenyl)methyl]piperazinyl}ethan-1-one.

16. A compound according to claim 1, which is 1-[(4b, 8a-cis-5,6,7,8,9,4b,8a-heptahydro-4aH-carbazol-9-yl) ethyl]-2-{4-[(4-isopropylphenyl)methyl]piperazinyl}ethan-1-one.

17. A compound according to claim 8, which is methyl (2S)-1-(2-{4-[(4-chlorophenyl)methyl]piperazinyl}indoline-2-carboxylate.

18. A compound according to claim 8, which is methyl (2S)-1-(2-{4-[(4-methylphenyl)methyl]piperazinyl}indoline-2-carboxylate.

19. A compound according to claim 8, which is methyl (2S)-1-(2-{4-[(4-ethylphenyl)methyl]piperazinyl}indoline-2-carboxylate.

20. A compound according to claim 8, which is methyl (2S)-1-(2-{4-[(4-isopropylphenyl)methyl]piperazinyl}indoline-2-carboxylate.

21. A compound according to claim 8, which is methyl (2R)-1-(2-{4-[(4-chlorophenyl)methyl]piperazinyl}indoline-2-carboxylate.

22. A compound according to claim 8, which is methyl (2R)-1-(2-{4-[(4-methylphenyl)methyl]piperazinyl}indoline-2-carboxylate.

23. A compound according to claim 8, which is (2S)-1-(2-{4-[(4-methylphenyl)methyl]piperazinyl}acetyl)indoline-2-carboxylic acid.

24. A compound according to claim 8, which is (2R)-1-(2-{4-[(4-chlorophenyl)methyl]piperazinyl}acetyl)indoline-2-carboxylic acid.

25. A compound according to claim 8, which is [(2S)-1-(2-{4-[(4-methylphenyl)methyl]piperazinyl}acetyl)indoline-2-yl]-N,N-dimethylcarboxamide.

26. A compound according to claim 8, which is 1-[(2S)-2-(hydroxymethyl)indolinyl]-2-{4-[(4-chlorophenyl)methyl]piperazinyl}ethan-1-one.

27. A compound according to claim 8, which is 1-[(2S)-2-(hydroxymethyl)indolinyl]-2-{4-[(4-methylphenyl)methyl]piperazinyl}ethan-1-one.

28. A compound according to claim 8, which is 1-[(2S)-2-(hydroxymethyl)indolinyl]-2-{4-[(4-ethylphenyl)methyl]piperazinyl}ethan-1-one.

29. A compound according to claim 8, which is 1-[(2S)-2-(hydroxymethyl)indolinyl]-2-{4-[(4-isopropylphenyl)methyl]piperazinyl}ethan-1-one.

30. A compound according to claim 8, which is 1-[(2S)-2-(methoxymethyl)indolinyl]-2-{4-[(4-chlorophenyl)methyl]piperazinyl}ethan-1-one.

31. A compound according to claim 8, which is 1-[(2S)-2-(methoxymethyl)indolinyl]-2-{4-[(4-methylphenyl)methyl]piperazinyl}ethan-1-one.

32. A compound according to claim 8, which is 1-((2S)-2-vinylindolinyl)-2-{4-[(4-chlorophenyl)methyl]piperazinyl}ethan-1-one.

33. A compound according to claim 8, which is 1-((2S)-2-vinylindolinyl)-2-{4-[(4-methylphenyl)methyl]piperazinyl}ethan-1-one.

34. A compound according to claim 8, which is 1-((2S)-2-(fluoromethylindolinyl)-2-{4-[(4-chlorophenyl)methyl]piperazinyl}ethan-1-one.

35. A compound according to claim 8, which is 1-((2S)-2-(fluoromethylindolinyl)-2-{4-[(4-methylphenyl)methyl]piperazinyl}ethan-1-one.

36. A compound according to claim 8, which is 1-((2S)-2-(difluoromethylindolinyl)-2-{4-[(4-chlorophenyl)methyl]piperazinyl}ethan-1-one.

37. A compound according to claim 8, which is 1-((2S)-2-(difluoromethylindolinyl)-2-{4-[(4-methylphenyl)methyl]piperazinyl}ethan-1-one.

38. A compound according to claim 8, which is 1-{(2S)-2-[(dimethylamino)methyl]indolinyl}-2-{4-[(4-chlorophenyl)methyl]piperazinyl}ethan-1-one.

39. A compound according to claim 8, which is 1-{(2S)-2-[(dimethylamino)methyl]indolinyl}-2-{4-[(4-methylphenyl)methyl]piperazinyl}ethan-1-one.

40. A pharmaceutical composition comprising a compound according to claim 1, together with at least one pharmaceutically acceptable carrier or excipient.

41. A pharmaceutical composition comprising a compound according to claim 8, together with at least one pharmaceutically acceptable carrier or excipient.

42. A method for the treatment of schizophrenia or Parkinson's disease, the method comprising administering to a patient in need of such treatment a therapeutically effective amount of a compound of claim 1.

43. A method for the treatment of schizophrenia or Parkinson's disease, the method comprising administering to a patient in need of such treatment a therapeutically effective amount of a compound of claim 8.

* * * * *